United States Patent
Wicker et al.

(10) Patent No.: US 11,254,650 B1
(45) Date of Patent: Feb. 22, 2022

(54) USE OF PNICTOGENIUM COMPOUNDS IN CARBON-CARBON BOND FORMATION

(71) Applicants: Southeastern Louisiana University, Hammond, LA (US); Fort Hays State University, Hays, KS (US)

(72) Inventors: Benjamin F. Wicker, Hammond, LA (US); Bruce A. Atwater, Hays, KS (US); Skyler A. Markham, Hays, KS (US)

(73) Assignees: Southeastern Louisiana University, Hammond, LA (US); Fort Hays State University, Hays, KS (US)

( * ) Notice: Subject to any disclaimer, the term of this patent is extended or adjusted under 35 U.S.C. 154(b) by 0 days.

(21) Appl. No.: 16/899,293

(22) Filed: Jun. 11, 2020

Related U.S. Application Data

(60) Provisional application No. 62/859,991, filed on Jun. 11, 2019.

(51) Int. Cl.
*C07D 401/04* (2006.01)
*C07D 213/127* (2006.01)

(52) U.S. Cl.
CPC ....... *C07D 401/04* (2013.01); *C07D 213/127* (2013.01)

(58) Field of Classification Search
CPC .................................................. C07D 401/04
See application file for complete search history.

(56) References Cited

PUBLICATIONS

Araki, Gass, Wicker, "Novel synthesis of 2,2'-bipyridine", Am. Chem. Soc. Southeastern Regional Meeting, 2017.
Atwater, "Synthesis of 2,2'-Bipyridines and Their Derivatives by the use of a Mild Phosphorus Extrusion Method," Am. Chem. Soc. Midwest Regional Meeting, 2018.
Bowen, Fernandes, Gitari, Layh, "Synthesis and Characterization of Alkyltris (2-pyridyl) phosphonium Salts," Phosphorus, Sulfur, and Silicon, 2006, 181:1403-1418.
Boyle, Hilton, McNally, "Nonsymmetrical Bis-Azine Biaryls from Chloroazines: A Strategy Using Phosphorus Ligand-Coupling," J. Am. Chem. Soc., 2019, 141, 15441 15449.
Dolewski, Hilton, McNally, "4-Selective Pyridine Functionalization Reactions via Heterocyclic Phosphonium Salts," Synlett, 2018, 29, 8-14.
Hilton, Dolewski, McNally, "Selective Functionalization of Pyridines via Heterocyclic Phosphonium Salts," J. Am. Chem. Soc., 2016, 138, 13806-13809.
Hilton, Zhang, Boyle, Alegre-Requena, Paton, McNally, "Heterobiaryl synthesis by contractive C-C coupling via P (V) intermediates," Science, 2018, 362, 799-804.
Hoffman, Howell, Muetterties, "Molecular Orbital Theory of Pentacoordinate Phosphorus," J. Am. Chem. Soc., 1972, 94, 3047-3058.
Horner, Hoffmann, "Quartare Arylphosphoniumsalze nach der,, Kobaltsalz-Methode" Chem. Ber., 1958, 91, 50-52 Concise explanation found in Specification, paragraph [0004].
Horner, Hoffmann, Wipple, Hassel, "Zum Spaltungsverlauf gemischt substituierter Tetraaryl-phosphonium-hydroxyde," Chem. Ber., 1958, 91, 52-57 Concise explanation found in Specification, paragraph [0004].
Horner, Mummenthey, Moser, Beck, "Die Einfuhrung von Arylresten in tertiare Phosphine mit Hilfe von Komplexen der Ubergangsmetalle (Komplexsalzmethode)" Chem. Ber., 1966, 99, 2782-2788 Concise explanation found in Specification, paragraph [0004].
Horner, Moser, "Beitrag zum Mechanismus der Arylphosphoniumsalzbildung aus tertiaren Phosphinen nach der ,, Kobaltsalz-Method," Chem. Ber., 1966, 99, 2789-2802 Concise explanation found in Specification, paragraph [0004].
Koniarczyk, Greenwood, Alegre-Requena, Paton, McNally, "A Pyridine-Pyridine Cross-Coupling Reaction via Dearomatized Radical Intermediates," Angew Chem. Int. Ed. 2019, 58(42), 14882-14886.
Markham, Araki, Wicker, Atwater, "Synthesis of 2,2'-bipyridine derivatives via a phosphorus extrusion," Am. Chem. Soc. Midwest Regional Meeting, Oct. 2018.
Mečiaorová, Toma, Loupy, Horv áth, "Synthesis of Phosphonium Salts—Phosphine Structure and Inorganic Salts Effects," Phosphorus, Sulfur, and Silicon and the Related Elements, 2008, 183:1, 21-33.
Newkome, Hager, "A New Contractive Coupling Procedure. Convenient Phosphorus Expulsion Reaction," J. Am. Chem. Soc., 1978, 100:17, 5567-5568.

(Continued)

*Primary Examiner* — Paul V Ward
(74) *Attorney, Agent, or Firm* — Jones Walker LLP

(57) ABSTRACT

A method of synthesizing a reaction product of the formula $R_3$-$R_4$ by reacting a pnictogenium salt of the formula

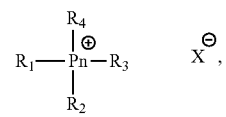

including a phosphonium salt of the formula

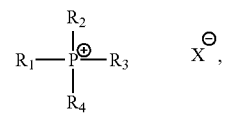

with a Lewis acid in the presence of a nucleophile. The reaction products can then be isolated for use. $R_1$ and $R_2$ are individually selected from the group consisting of hydrogen, alkyl, heteroalkyl, aryl, heteroaryl, aralkyl, alkoxy, amino, and organosilyl. $R_3$ and $R_4$ are individually selected from the group consisting of optionally substituted monocyclic or polycyclic heteroaromatic moieties, optionally substituted monocyclic or polycyclic heteroaliphatic moieties, and optionally substituted linear or branched heteroaliphatic moieties. $R_1$ or $R_2$ optionally forms a covalent bond with $R_3$ or $R_4$. X is an anion.

26 Claims, 13 Drawing Sheets

(56) References Cited

PUBLICATIONS

Patel, Mohnike, Hilton, McNally, "A Strategy to Aminate Pyridines, Diazines, and Pharmaceuticals via Heterocyclic Phosphonium Salts," Org. Lett. 2018, 20, 2607-2610.
Uchida, Onoue, Tada, Nagao, Oae, "Ligand Coupling Reaction on the Phosphorus Atom," Tetrahedron Lett., 1989, 30:5, 567-570.
Uchida, Kozawa, Oae, "Formation of 2,2'-Bipyridyl by Ligand Coupling on the Phosphorus Atom," Tetrahedron Lett., 1989, 30:46, 6365-6368.
Uchida, Kajita, Kawasaki, Oea, "Unusual Formation of 5-Halo-2,2'-Bipyridyls by Treatment of Tris(2-Pyridyl) Phosphine Derivatives with Halogens," Tetrahedron Lett., 1995, 36:23, 4077-4080.
Wicker, Gass, Lawrence, Wang, Davis, Sykora, "Synthesis of Novel Phosphonium Ligands," Am. Chem. Soc. Spring Nat'l Mtg., San Diego, CA, 2016.
Zhang, McNally, "Phosphonium Salts as Pseudohalides: Regioselective Nickel-Catalyzed Cross-Coupling of Complex Pyridines and Diazines," Angew. Chem., Int. Ed. 2017, 56, 9833-9836.
Zhmurova, Kosinskaya, Pinchuk, "Phosphorylation of heterocyclic compounds" Zh. Obshch. Khim., 1981, 51:7, 1538-1541 Concise explanation found in Specification, paragraph [0004].

USE OF PNICTOGENIUM COMPOUNDS IN CARBON-CARBON BOND FORMATION

CROSS-REFERENCE TO RELATED APPLICATIONS

This application claims the benefit of U.S. Provisional Application No. 62/859,991, filed Jun. 11, 2019, which is incorporated herein in its entirety by reference.

BACKGROUND

The present disclosure relates to the synthesis of industrially useful compounds via pnictogenium extrusion of pnictogenium salts, including phosphorus extrusion of phosphonium salts. The compounds produced include, but are not limited to, bis-heterocycle compounds.

The class of bis-heterocycle compounds generated have been extremely difficult to synthesize via more traditional transition metal catalyzed routes because the heterocycles tend to bind to the metal center, poisoning the catalyst. An example of the reaction product synthesized is 2,2'-bipyridine ("bipy"), which is a popular ligand in coordination chemistry. Functionalization of bipy and other bis-heterocycle compounds allows the fine tuning of the chemical properties of complexes formed with those compounds. For example, functionalized bis-heterocycle complexes have become increasingly important in technologies such as solar energy. A simple effective synthesis of these ligands will be increasingly important.

Phosphonium salts with one, two, and three heteroaromatic rings have been reported. Early research regarding the synthesis of phosphonium compounds used nucleophilic substitution with phosphines and alkyl or aryl bromides via cobalt catalyst. Horner, Hoffmann, Chem. Ber., 1958, 91, 50; Horner, Hoffmann, Wipple, Hassel, Chem. Ber., 1958, 91, 52; Horner, Mummenthey, Moser, Beck, Chem. Ber., 1966, 99, 2782; Horner, Moser, Chem. Ber., 1966, 99, 2789. More recent research on phosphonium cations included the synthesis of triphenyl-2-pyridylphosphonium (i.e., [P(C$_6$H$_5$)$_3$(2-C$_5$H$_4$N)]$^+$ or "[Mopyphos]$^+$") and related phosphonium salts without a solvent or catalyst. Zhmurova, Kosinskaya, Pinchuk, Zh. Obshch. Khim., 1981, 51, 1538. The [Mopyphos]$^+$ synthesis was later improved by incorporating salts into the heating process to generate phosphonium salts of various anions. Mečiaorová, Toma, Loupy, and Horváth, Phosphorus, Sulfur Silicon Relat. Elem., 2008, 183, 21. Both of these processes utilized triphenylphosphine to perform a nucleophilic substitution of 2-bromopyridine to generate [Mopyphos]Br, with the later research also incorporating a salt during the synthesis to allow for the formation of phosphonium salts of different anions. A more recent example of phosphonium synthesis utilizes triflic anhydride and is selective for the generation of 4-pyridyl phosphonium salts. Hilton, Dolewski, McNally, J. Am. Chem. Soc., 2016, 138, 13806.

Phosphonium salts with only two heteroaromatic rings have been reported. In one example, the diphenyl-bis-(2-pyridyl)phosphonium cation (i.e., [P(C$_6$H$_5$)$_2$(2-C$_5$H$_4$N)$_2$]$^+$ or "[Dipyphos]$^+$") was produced in [Dipyphos]Br. Wicker, Gass, Lawrence, Wang, Davis, Sykora, Synthesis of novel phosphonium ligands, Am. Chem. Soc. Spring Nat'l Mtg., San Diego, Calif., 2016. Later reports by other researchers disclosed phosphonium salts with two heteroaromatic rings.

The synthesis of bipy compounds in prior research required high temperatures or harsh conditions. For example, one research group used various phosphine, phosphine oxide, and one example of a mixed aryl/alkyl phosphonium compound as starting materials, but their conditions required either high temperatures (reflux) or harsh reagents (elemental halide). Uchida, Onoue, Tada, Nagao, Oae, Tetrahedron Lett., 1989, 30, 567; Uchida, Kozawa, Oae, Tetrahedron Lett., 1989, 30, 6365; Uchida, Kajita, Kawasaki, Oea, Tetrahedron Lett., 1995, 36, 4077. Likewise, another researcher's phosphorus extrusion occurs under strongly acidic conditions and the relatively high temperature of 80° C. Hilton, Dolewski, McNally, J. Am. Chem. Soc., 2016, 138, 13806; Zhang, McNally, Angew. Chem., Int. Ed., 2017, 56, 9833; Patel, Mohnike, Hilton, McNally, Org. Lett., 2018, 20, 2607; Dolewski, Hilton, McNally, Synlett, 2018, 29, 08; Hilton, Zhang, Boyle, Alegre-Requena, Paton, McNally, Science 2018, 362, 799-804. Another example used a nucleophile (NaOR) and a high temperature of 100° C. Newkome, Hager, J. Am. Chem. Soc., 1978, 100, 5567. Still another example used milder conditions, but required the presence of three pyridyl rings to ensure the proper orientation of the pyridyl rings for extrusion. Bowen, Fernandes, Gitari, Layh, Phosphorours, Sulfur, Silicon Relat. Elem., 2006, 181, 1403.

The method of bipy formation disclosed herein is unique from each of these in that it utilizes mild conditions (generally an amine, nucleophile, metal Lewis acid, and room temperature), and isolates the pnictogenium or phosphonium intermediate. This method of pnictogenium salt synthesis extends to other anions besides bromine, as well as beyond triphenylphosphine and 2-bromopyridine.

SUMMARY

A process for synthesizing a compound of the formula R$_3$-R$_4$, including but not limited to bis-heterocyclic compounds, involves pnictogen extrusion from pnictogenium salts, including phosphorus extrusion from phosphonium salts. First, the pnictogenium salts may be synthesized via a substitution mechanism under solvent-free conditions resulting in good yields. Optionally, the anions in the pnictogenium salts may be exchanged for other anions. The salts of the formula

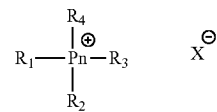

undergo pnictogen extrusion in the presence of a Lewis acid and a nucleophile. This extrusion occurs with varying yields of the coupled products and is promoted by the binding of N-heterocycles to a Lewis acid, in the presence of a nucleophile. The reaction products can then be isolated for use.

The above summary is not intended to describe each illustrated embodiment or every possible implementation. These and other features, aspects, and advantages of the present invention will become better understood with regard to the following description and claims.

BRIEF DESCRIPTION OF THE DRAWINGS

The accompanying figures, which, together with the detailed description below, are incorporated in and form part of the specification, serve to illustrate further various embodiments and to explain various principles and advantages in accordance with the present invention.

DETAILED DESCRIPTION OF SELECTED EMBODIMENTS

Figure 1:
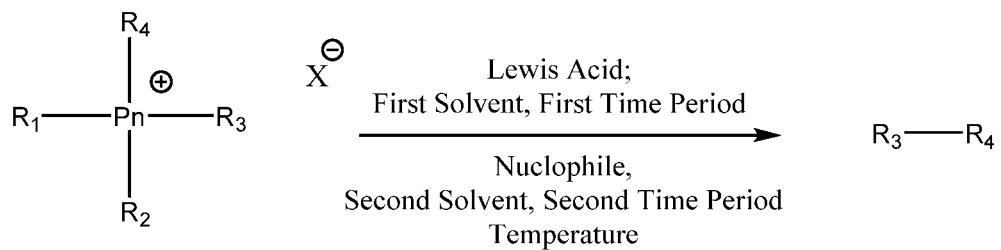
FIG. 1 illustrates the synthesis of the reaction product from a pnictogenium salt.

Detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Alternate embodiments may be devised without departing from the spirit or the scope of the invention. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures.

Exemplary embodiments of the present invention are described below.

A reaction product of the formula $R_3$-$R_4$ may be synthesized by reacting a pnictogenium salt of the formula

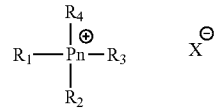

with a Lewis acid, in the presence of a nucleophile. $R_1$ and $R_2$ are individually selected from the group consisting of hydrogen, alkyl, heteroalkyl, aryl, heteroaryl, aralkyl, alkoxy, amino, and organosilyl. $R_3$ and $R_4$ are individually selected from the group consisting of optionally substituted moncyclic or polycyclic heteroaromatic moieties, optionally substituted monocyclic or polycyclic heteroaliphatic moieties, and optionally substituted linear or branched heteroaliphatic moieties. In some embodiments, $R_1$ or $R_2$ forms a covalent bond with $R_3$ or $R_4$. X is an anion. Pn is a pnictogen, including nitrogen, phosphorus, arsenic, antimony, bismuth, and moscovium.

With reference to FIG. 1, one exemplary reaction procedure includes dissolving the pnictogenium salt in a first solvent with X molar equivalents of a Lewis acid. This solution may be stirred for a first time period. Y molar equivalents of a nucleophile may be dissolved in a second solvent to form a nucleophile solution. After the first time period, the nucleophile solution may be added dropwise to the stirring solution over five minutes. Stirring may then continue for a second time period. After the second time period, the reaction product of the formula $R_3$-$R_4$ may be purified.

In some embodiments, a reaction product of the formula $R_3$-$R_4$ may be synthesized by reacting a phosphonium salt of the formula

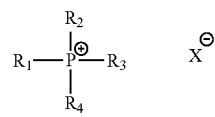

with a Lewis acid, in the presence of a nucleophile. $R_1$ and $R_2$ are individually selected from the group consisting of hydrogen, alkyl, heteroalkyl, aryl, heteroaryl, aralkyl, alkoxy, amino, and organosilyl. $R_3$ and $R_4$ are individually selected from the group consisting of optionally substituted moncyclic or polycyclic heteroaromatic moieties, optionally substituted monocyclic or polycyclic heteroaliphatic moieties, and optionally substituted linear or branched heteroaliphatic moieties. In some embodiments, $R_1$ or $R_2$ forms a covalent bond with $R_3$ or $R_4$. X is an anion.

Figure 2:
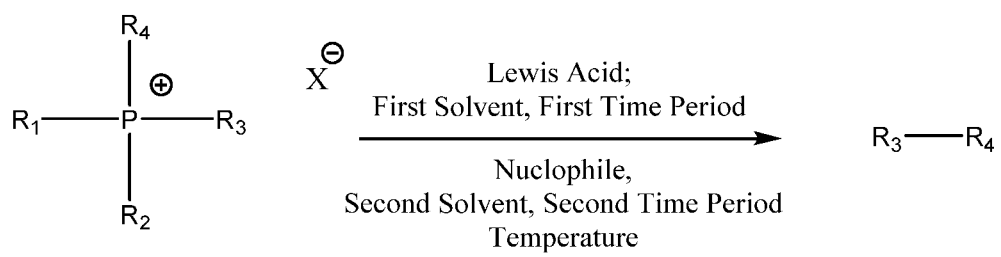
FIG. 2 illustrates the synthesis of the reaction product from a phosphonium salt.

With reference to FIG. 2, one exemplary reaction procedure involves dissolving the phosphonium salt in a first solvent with X molar equivalents of a Lewis acid. This solution may be stirred for a first time period. Y molar equivalents of a nucleophile may be dissolved in a second solvent to form a nucleophile solution. After the first time period, the nucleophile solution may be added dropwise to the stirring solution over five minutes. Stirring of the reaction mixture may then continue for a second time period. After the second time period, the reaction product of the formula $R_3$-$R_4$ may be purified.

In the embodiments illustrated in FIGS. 1 and 2, the Lewis acid may be $H^+$, a monovalent metal, a divalent metal, or a trivalent metal. The nucleophile may be a primary, secondary, or tertiary amine. The reaction may occur at ambient temperature, such as a temperature in the range of 20° C. to 30° C., or any subrange therein. Alternatively, the reaction may occur at a temperature above or below ambient temperature, such as a temperature in the range of −5° C. to 80° C., or any subrange therein. In some embodiments, the yield of the reaction product $R_3$-$R_4$ may be greater than 20%. The yield of the reaction product $R_3$-$R_4$ of greater than 20% may be achieved in less than 72 hours, less than 36 hours, less than 24 hours, less than 12 hours, less than 8 hours, less than 4 hours, or less than 1 hour, or any subrange therein. In other embodiments, the yield of the reaction product $R_3$-$R_4$ may be greater than 30%, greater than 40% or greater than 50%. In still other embodiments, the yield of the reaction product $R_3$-$R_4$ may be greater than 10%. In some embodiments, $R_1$ is not a heteroaromatic group and $R_2$ is not a heteroaromatic group. In certain embodiments, $R_1$ and $R_2$, taken together, form an optionally substituted ring consisting of 3-10 backbone atoms, with the ring optionally comprising one or two heteroatoms beyond the pnictogen to which $R_1$ and $R_2$ are bonded.

The synthesis of the reaction product $R_3$-$R_4$ was demonstrated in a series of experiments. For example, $[Dipyphos]^+$ salts were used to synthesize 2,2'-bipyridine.

Example 1

Figure 3:
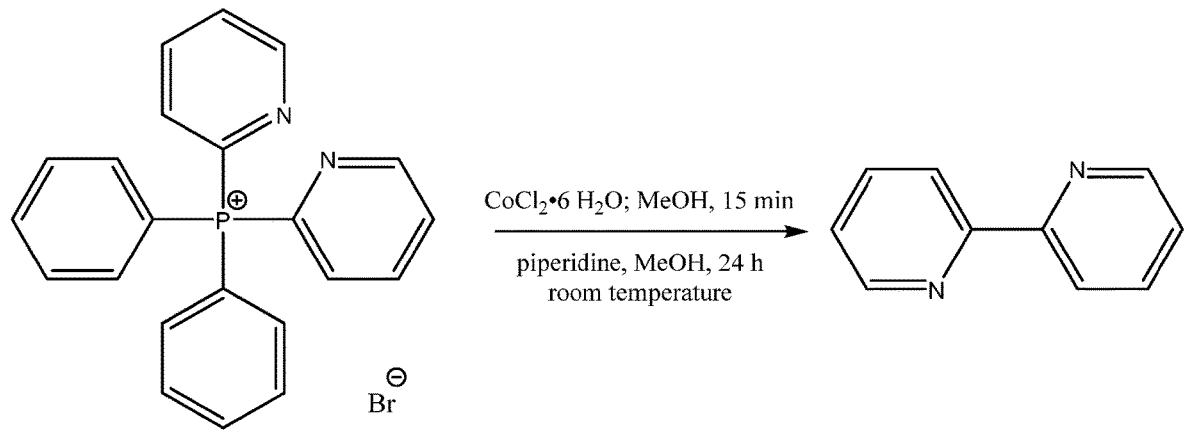
FIG. 3 illustrates the synthesis of the reaction product described in Example 1.

With reference to FIG. 3 and Table 1 below, experiments were conducted to evaluate the yield of the reaction product $R_3$-$R_4$ when the amount of the Lewis acid and the amount of the nucleophile were varied. Specifically, 0.24 mmol of [Dipyphos]Br was dissolved in 5 mL of methanol with X molar equivalents of the Lewis acid $CoCl_2 \cdot 6H_2O$ (X=1-10 molar equivalents of the Lewis acid). The solution was stirred for 15 minutes. After this time, Y molar equivalents of the nucleophile piperidine (Y=1-10 molar equivalents of the nucleophile) was dissolved in 5 mL of methanol to form a nucleophile solution. The nucleophile solution was added dropwise to the stirring solution over five minutes. Stirring of the reaction mixture was then continued for 24 hours.

The following purification procedure was then implemented: The reaction mixture was diluted with 30 mL of the solvent dichloromethane and the organic layer was washed twice with 15 mL of 0.10 M $Na_2EDTA$. The organic layer was dried with $Na_2SO_4$ and the solvent was removed in vacuo. The resulting clear, colorless to slightly yellow oil was purified by flash column chromatography (95:5 hexanes/ethyl acetate) yielding the reaction product bipyridine. If no transition metal was used, the solution was washed once with 0.1 M aqueous $NaHCO_3$ and twice with 25 mL portions of distilled water. Additionally, the first aqueous wash was washed once with 25 mL of the solvent dichloromethane. The organic fractions were combined, and the solvent removed. The entire procedure described in this Example 1 was conducted at ambient temperature.

The isolated product was analyzed by $^1H$ NMR and GCMS to verify its composition. The isolated yields of the reaction product for various X and Y conditions (i.e., various amounts of the Lewis acids and the nucleophile, respectively) are reported in Table 1 below.

TABLE 1

| For X = Y = 1; yield (26%) | For X = Y = 2; yield (27%) | For X = Y = 3; yield (20%) |
|---|---|---|
| For X = Y = 4; yield (38%) | For X = Y = 5; yield (43%) | For X = Y = 6; yield (22%) |

TABLE 1-continued

| For X = Y = 10; yield (14%) | For X = 5, Y = 1; yield (34%) | For X = 1, Y = 2; yield (2%) |
|---|---|---|

Example 2

Figure 4:
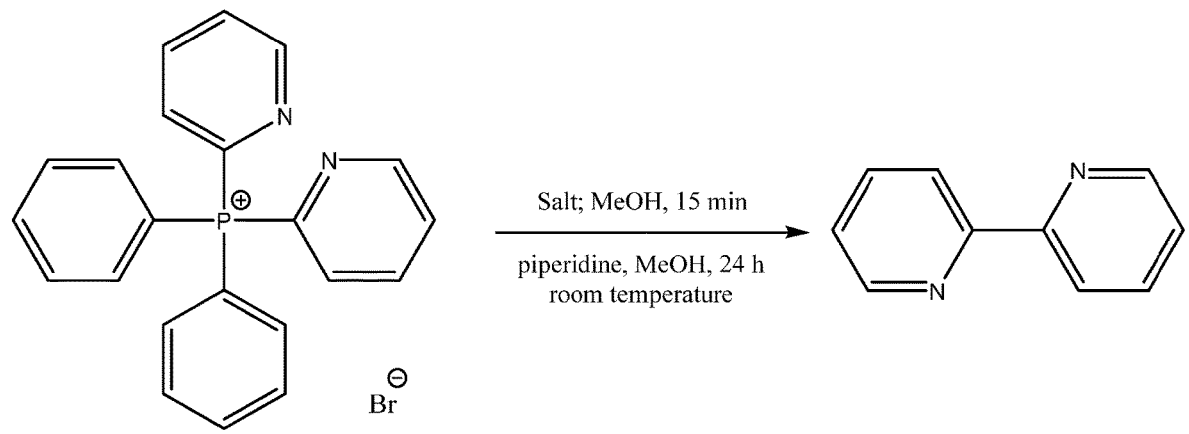
FIG. 4 illustrates the synthesis of the reaction product described in Example 2.

Referring now to FIG. 4 and Table 2 below, experiments were conducted to evaluate the yield of the reaction product $R_3$-$R_4$ when the Lewis acid was varied. Specifically, 0.24 mmol of [Dipyphos]Br was dissolved in 5 mL of methanol with the one or five molar equivalents of each of the Lewis acid salts listed in Table 2. The solution was stirred for 15 min. After this time, an equimolar amount of nucleophile piperidine was dissolved in 5 mL of methanol to form a nucleophile solution. The nucleophile solution was added dropwise to the stirring solution over five minutes. Stirring of the reaction mixture was continued for 5-24 hours. The purification procedure of Example 1 was then implemented. The entire procedure described in this Example 2 was conducted at ambient temperature. The isolated product was analyzed by $^1H$ NMR and GCMS to verify its composition. The isolated yields of the reaction product for various Lewis acids with both 1:1 and 5:5 molar ratios of Lewis acid/nucleophile are reported in Table 2 below.

TABLE 2

| 1:1 Lewis Acid/Piperidine | 5:5 Lewis Acid/Piperidine |
|---|---|
| For $CoCl_2 \cdot 6H_2O$, 5 h stirring; yield (21%) | For $CoCl_2 \cdot 6H_2O$, 24 h stirring; yield (42%) |
| For LiCl, 5 h stirring; yield (1.6%) | For LiCl, 24 h stirring; yield (0%) |
| For NaCl, 5 h stirring; yield (9.8%) | For NaCl, 24 h stirring; yield (11%) |
| For KCl, 5 h stirring; yield (5.6%) | For KCl, 5 h stirring; yield (31%) |
| For $MgCl_2 \cdot 6H_2O$, 5 h stirring; yield (0.6%) | For $MgCl_2 \cdot 6H_2O$, 24 h stirring; yield (2%) |
| For $CaCl_2 \cdot 2H_2O$, 5 h stirring; yield (20%) | For $CaCl_2 \cdot 2H_2O$, 24 h stirring; yield (5%) |
| For $SrCl_2 \cdot 6H_2O$, 5 h stirring; yield (15%) | For $SrCl_2 \cdot 6H_2O$, 5 h stirring; yield (0%) |
| For $BaCl_2 \cdot 2H_2O$, 5 h stirring; yield (10%) | For $BaCl_2 \cdot 2H_2O$, 24 h stirring; yield (0%) |
| For $FeCl_2 \cdot 4H_2O$, 5 h stirring; yield (15%) | For $FeCl_2 \cdot 4H_2O$, 24 h stirring; yield (3%) |
| For $FeCl_3 \cdot 6H_2O$, 5 h stirring; yield (0%) | For $FeCl_3 \cdot 6H_2O$, 24 h stirring; yield (0%) |
| For $NiCl_2 \cdot 6H_2O$, 5 h stirring; yield (4%) | For $NiCl_2 \cdot 6H_2O$, 24 h stirring; yield (14%) |
| For $CuCl_2 \cdot 2H_2O$, 5 h stirring; yield (8%) | For $CuCl_2 \cdot 2H_2O$, 24 h stirring; yield (31%) |

Example 3

Figure 5:
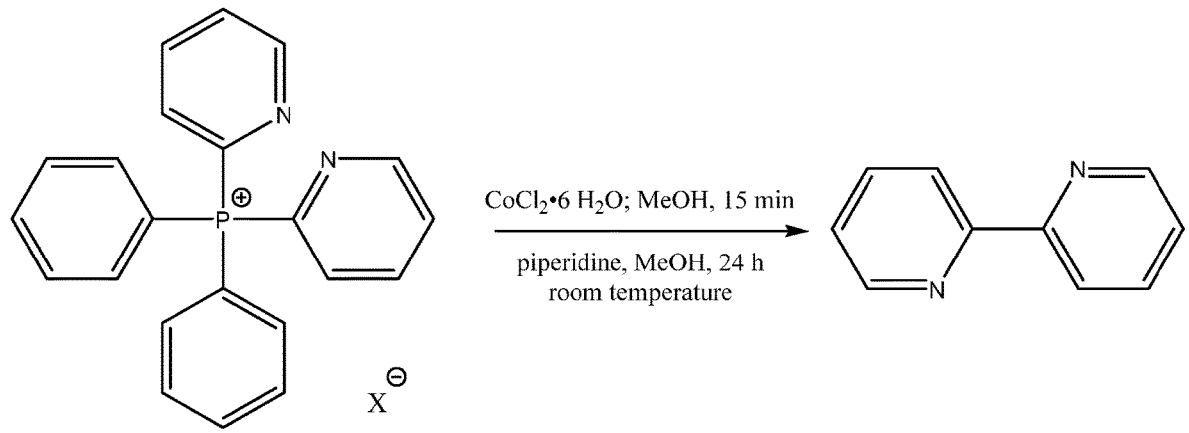
FIG. 5 illustrates the synthesis of the reaction product described in Example 3.

With reference now to FIG. 5 and Table 3 below, experiments were conducted to evaluate the yield of the reaction product $R_3$-$R_4$ when the anion X was varied. Specifically, 0.24 mmol of [Dipyphos]X was dissolved in 5 mL of methanol with the one molar equivalent of the Lewis acid $CoCl_2 \cdot 6H_2O$. X in this Example 3 refers to the various anions listed in Table 3 below. The solution was stirred for 15 min. After this time, one molar equivalent of the nucleophile piperidine was dissolved in 5 mL of methanol to form a nucleophile solution. The nucleophile solution was added dropwise to the stirring solution over five minutes. Stirring of the reaction mixture was continued for 24 hours. The purification procedure of Example 1 was then implemented. The entire procedure described in this Example 3 was conducted at ambient temperature. The isolated product was analyzed by $^1$H NMR and GCMS to verify its composition. The isolated yields of the reaction product for various anions are reported in Table 3 below.

TABLE 3

| For X = Br; yield (21%) | For X = BF$_4$; yield (0%) | For X = PF$_6$; yield (0%) |
|---|---|---|
| For X = OTf; yield (20%) | For X = NTf$_2$; yield (12%) | |

Example 4

Figure 6:
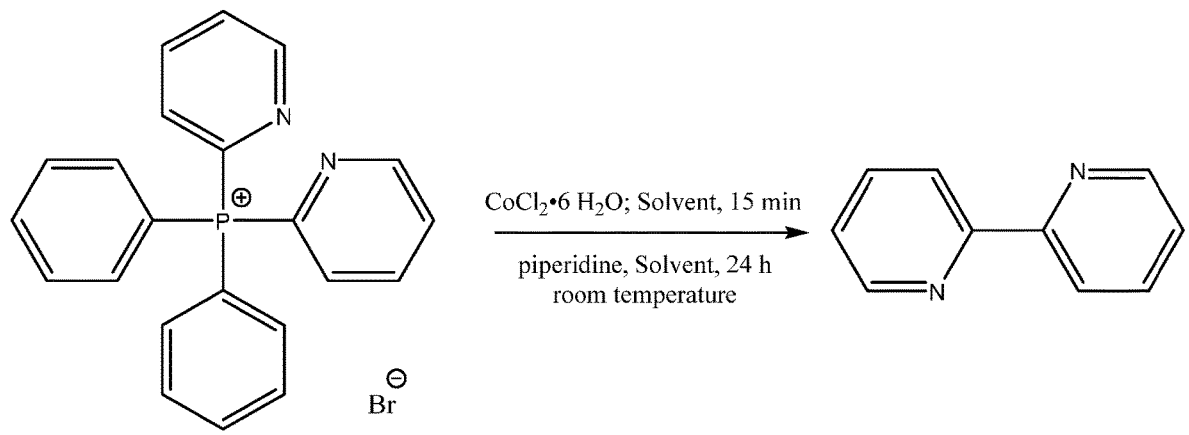
FIG. 6 illustrates the synthesis of the reaction product described in Example 4.

With reference to FIG. 6 and Table 4 below, experiments were conducted to evaluate the yield of the reaction product R$_3$-R$_4$ when various solvents were used. Specifically, 0.24 mmol of [Dipyphos]Br was dissolved in 5 mL of each of the solvents listed in Table 4 with five molar equivalents of the Lewis acid CoCl$_2$.6H$_2$O. The solution was stirred for 15 min. After this time, five molar equivalents of the nucleophile piperidine was dissolved in 5 mL of the same solvent to form a nucleophile solution. The nucleophile solution was added dropwise to the stirring solution over five minutes. Stirring of the reaction mixture was then continued for 24 hours. The purification procedure of Example 1 was then implemented. The entire procedure described in this Example 4 was conducted at ambient temperature. The isolated product was analyzed by $^1$H NMR and GCMS to verify its composition. The isolated yields of the reaction product for various solvents are reported in Table 4 below.

TABLE 4

| For methanol; yield (42%) | For ethanol (absolute); yield (20%) | For ethanol (95%); yield (18%) |
|---|---|---|
| For 2-propanol; yield (1%) | For dimethylformamide; yield (25%) | For water; yield (12%) |
| For dichloromethane; yield (0%) | For dimethylsulfoxide; yield (15%) | For 1,4-dioxane; yield (0%) |
| For acetone; yield (0%) | For tetrahydrofuran; yield (0%) | |

Example 5

Figure 7:
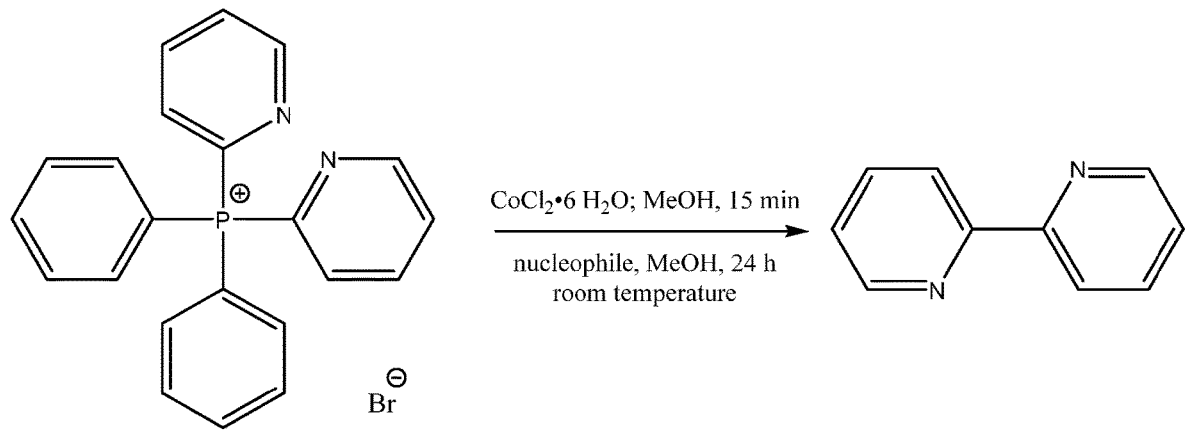
FIG. 7 illustrates the synthesis of the reaction product described in Example 5.

Referring now to FIG. 7 and Table 5 below, experiments were conducted to evaluate the yield of the reaction product R$_3$-R$_4$ when various nucleophiles were used. Specifically, 0.24 mmol of [Dipyphos]Br was dissolved in 5 mL of methanol with five molar equivalents of the Lewis acid CoCl$_2$.6H$_2$O. The solution was stirred for 15 min. After this time, five molar equivalents of each of the nucleophiles listed in Table 5 below was dissolved in 5 mL of methanol to form a nucleophile solution. The nucleophile solution was added dropwise to the stirring solution over five minutes. Stirring of the reaction mixture was continued for 24 hours. The purification procedure of Example 1 was then implemented. The entire procedure described in this Example 5 was conducted at ambient temperature. The isolated product was analyzed by $^1$H NMR and GCMS to verify its composition. The isolated yields of the reaction product for various nucleophiles are reported in Table 5 below.

TABLE 5

| For piperidine; yield (42%) | For sodium phenylsulfide; yield (0%) |
|---|---|
| For pyrollidine; yield (45%) | For N-methylpiperazine; yield (40%) |
| For triethylamine; yield (72%) | For diisopropylamine; yield (45%) |

TABLE 5-continued

| For butylamine; yield (48%) | For ethyldiisopropylamine; yield (34%) |
|---|---|
| For sodium carbonate; yield (45%) | For 2,2,6,6-tetramethylpiperidine; yield (22%) |
| For morpholine; yield (44%) | For sodium hydroxide; yield (3%) |
| For diethylamine; yield (51%) | |

Example 6

Figure 8:
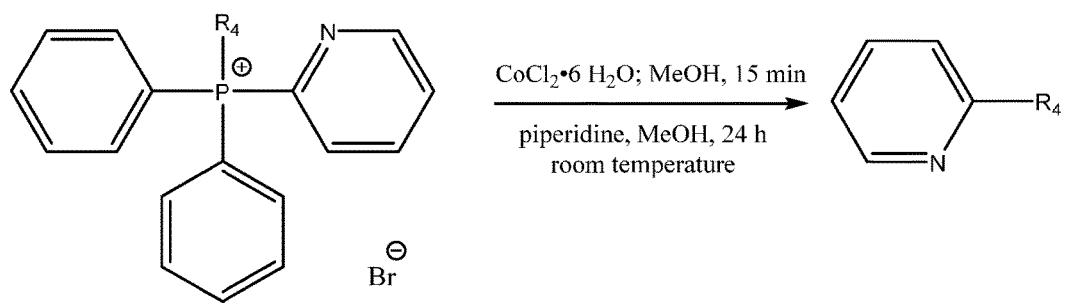
FIG. 8 illustrates the synthesis of the reaction product described in Example 6.

Referring now to FIG. 8 and Table 6 below, experiments were conducted to evaluate the yield of the reaction product R$_3$-R$_4$ when R$_3$ is 2-pyridyl and R$_4$ is a different heterocycle. Specifically, 0.24 mmol of the phosphonium salts formed with each of the R$_4$ groups in Table 6 was dissolved in 5 mL of methanol with five molar equivalents of the Lewis acid CoCl$_2$.6H$_2$O. The solution was stirred for 15 min. After this time, five molar equivalents of the nucleophile triethylamine was dissolved in an additional 5 mL of methanol to form a nucleophile solution. The nucleophile solution was added dropwise to the stirring solution over five minutes. Stirring of the reaction mixture was continued for 21 hours. The purification procedure of Example 1 was then implemented. The entire procedure described in this Example 6 was conducted at ambient temperature. The isolated products were analyzed by $^1$H NMR and GCMS to verify its composition. The isolated yields of the reaction product from the phosphonium salts with each R$_4$ group are reported in Table 6 below.

TABLE 6

| R$_4$ = 4-amino-2-pyridyl; yield (32%) | R$_4$ = 4-methyl-2-pyridyl; yield (93%) |
|---|---|

The experiments in Examples 1-6 were conducted at ambient temperature. Comparable yields of the reaction product are expected at temperatures in the range of 20° C. to 30° C., or any subrange therein. The synthesis of the reaction product R$_3$-R$_4$ described herein may be conducted at higher or lower temperatures, such as temperatures in the range of −5° C. to 5° C. or 75-85° C., or any subrange therein, with lower expected yields.

Example 7

Figure 9:
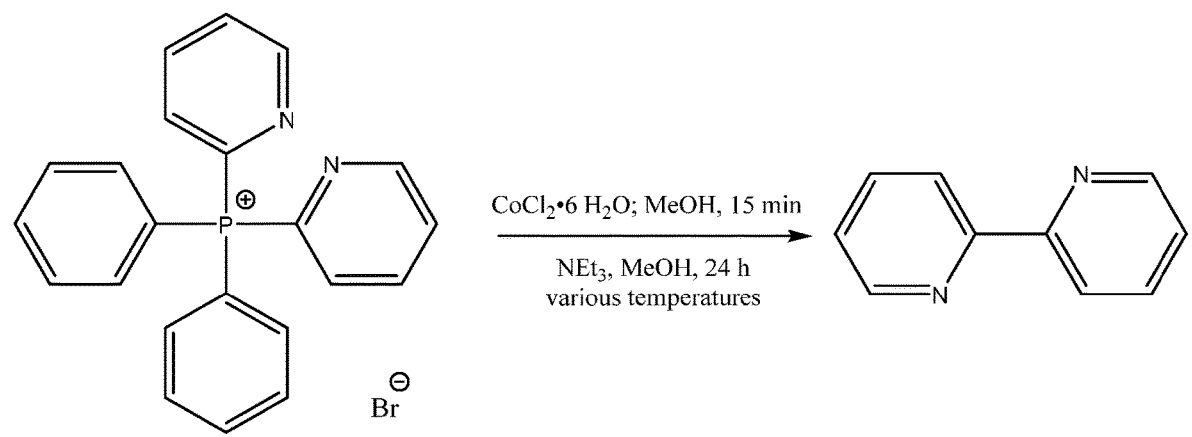
FIG. 9 illustrates the synthesis of the reaction product described in Example 7.

With reference to FIG. 9 and Table 7 below, experiments were conducted to evaluate the yield of the reaction product R$_3$-R$_4$ at different temperatures. Specifically, 0.24 mmol of [Dipyphos]Br was dissolved in 5 mL of methanol with five molar equivalents of the Lewis acid CoCl$_2$.6H$_2$O. The solution was stirred for 15 min, to allow for thermal equilibrium to establish. After this time, five molar equivalents of the nucleophile triethylamine was dissolved in an additional 5 mL of methanol to form a nucleophile solution. The nucleophile solution was added dropwise to the stirring solution over five minutes. Stirring of the reaction mixture was then continued for 24 hours at each of the designated temperatures in Table 7. The purification procedure of Example 1 was then implemented. The isolated product was analyzed by $^1$H NMR and GCMS to verify its composition. The isolated yield of the reaction product at each reaction temperature is reported in Table 7 below.

TABLE 7

| For 0° C.; yield (56%) | For room temperature; yield (72%) |
|---|---|
| For 80° C.; yield (26%) | |

The synthesis of 2,2'-bipyridine from the [Dipyphos]⁺ salts in Examples 1-7 demonstrates the method of synthesizing a reaction product $R_3$-$R_4$ from a phosphonium salt. These experiments show that phosphonium salts of the formula

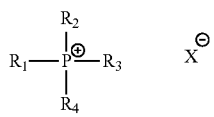

will react with Lewis acids in the presence of a nucleophile to synthesize various reaction products of the formula $R_3$-$R_4$ of the full scope of the method disclosed herein with analogous yields, as shown in Example 6. Based on the experiments in Examples 1-7, we also expect that other pnictogenium salts of the formula

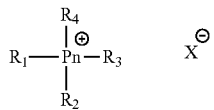

will react with Lewis acids in the presence of a nucleophile to synthesize various reaction products of the formula $R_3$-$R_4$ of the full scope of the method disclosed herein with analogous yields due to the similarity in properties of phosphorus atoms and the other pnictogen atoms. Specifically, the positive charge of all pnictogenium ions of this formula will attract the nucleophile, and the pnictogenic center should not affect the interactions between the Lewis acid and the heterocycles $R_3$ and/or $R_4$, which promote pnictogen extrusion. Additionally, the pnictogen-carbon bond is weaker for heavier pnictogen atoms, which should result in a more facile pnictogen extrusion to generate the reaction product $R_3$-$R_4$.

Figure 10:
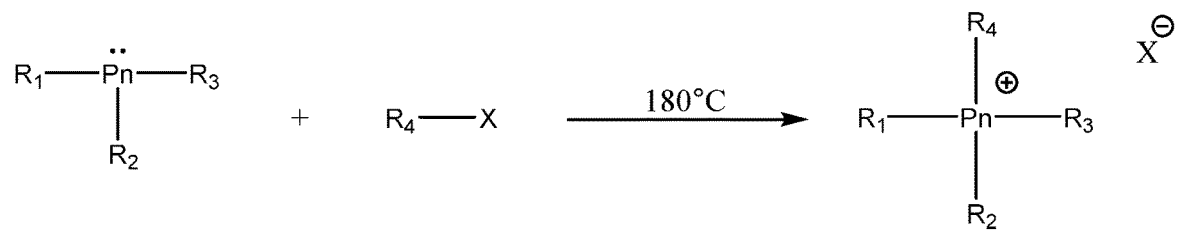
FIG. 10 illustrates the synthesis of pnictogenium salts.
Figure 11:
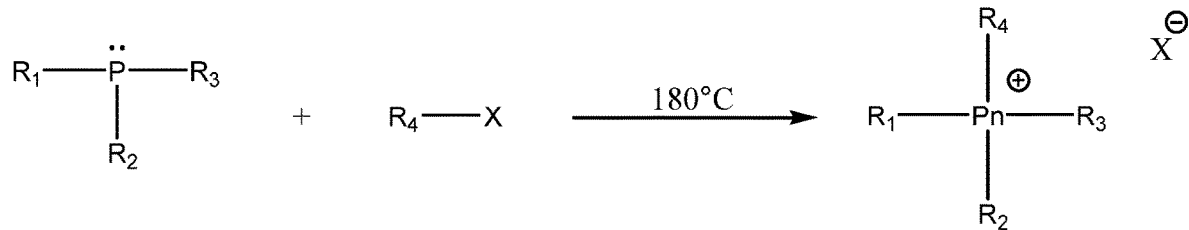
FIG. 11 illustrates the synthesis of phosphonium salts.

Referring now to FIGS. 10 and 11, the pnictogenium salts used in the synthesis described above may be produced by reacting a compound of the formula $Pn(R_1)(R_2)(R_3)$, including a compound of the formula $P(R_1)(R_2)(R_3)$ as shown in FIG. 11, with $R_4X$.

Example 8

Figure 12:
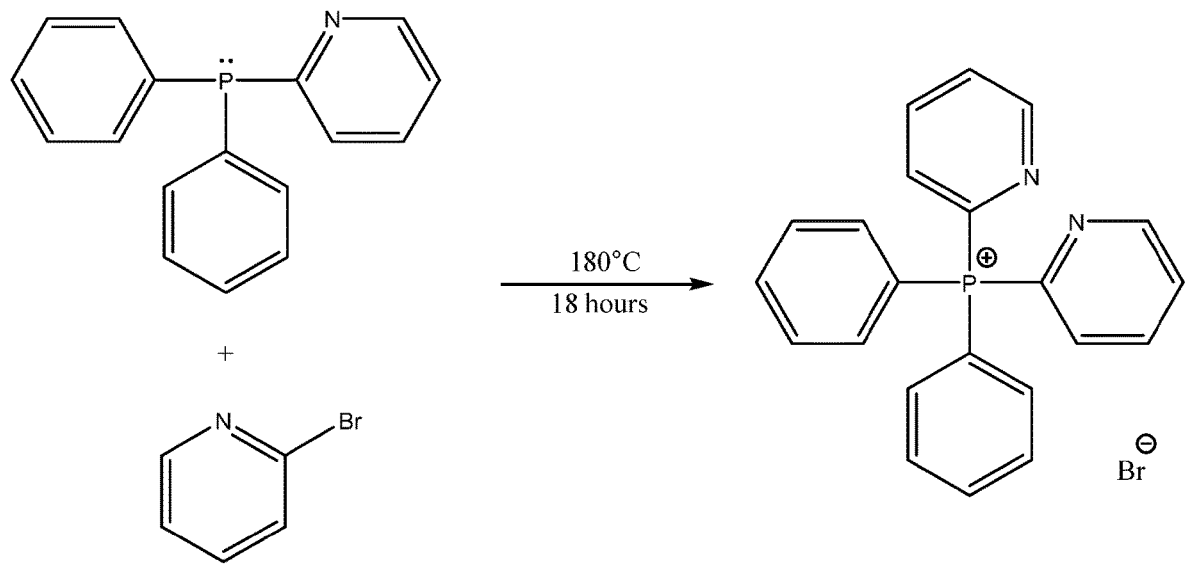
FIG. 12 illustrates the synthesis of the phosphonium salt described in Example 8.

With reference to FIG. 12, 19.8 mmol of diphenyl(2-pyridyl)phosphine was placed in a thick walled pressure vessel equipped with a Teflon screw cap. To this vessel was also added 19.8 mmol of 2-bromopyridine. The mixture was heated for 18 hours at 180° C. When the mixture was cooled, the residue was dissolved in dichloromethane and stirred with decolorizing carbon. The mixture was then filtered to remove the carbon, and the solution was concentrated. Diethyl ether was then added to the resulting solution until the product was precipitated. The yield of [Dipyphos]Br in this reaction was 88%. The reaction product was analyzed by $^1H$, $^{13}C$, and $^{31}P$ NMR, as well as X-ray crystallography.

Example 9

Figure 13:
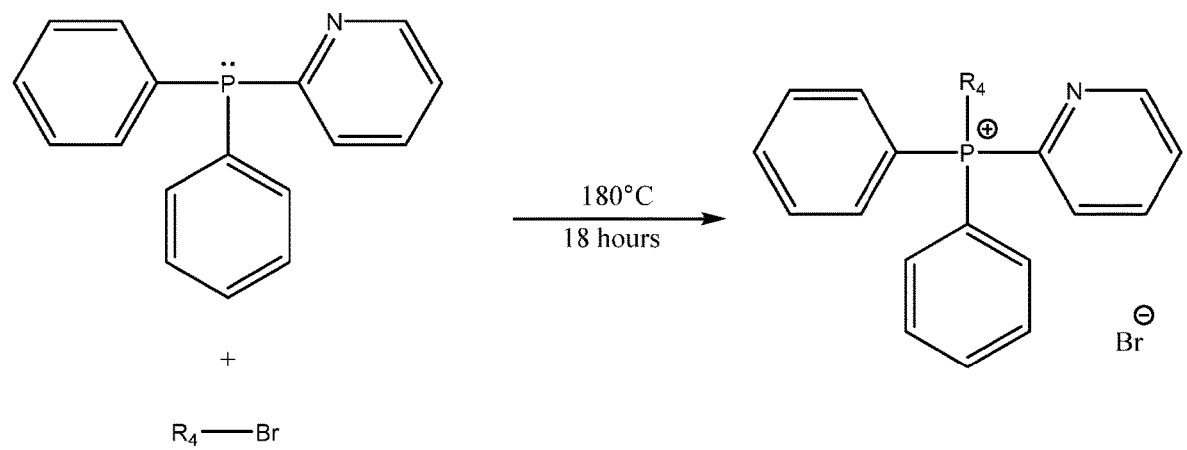
FIG. 13 illustrates the synthesis of the phosphonium salt described in Example 9.

Referring to FIG. 13 and Table 8 below, 4.0 mmol of diphenyl(2-pyridyl)phosphine was placed in a thick walled pressure vessel equipped with a Teflon screw cap. To this vessel was also added 4.0 mmol of each of the N-heterocycles listed in Table 8. The mixture was heated for 18 hours at 180° C. When the mixture was cooled, the residue was dissolved in methanol and stirred with decolorizing carbon. The mixture was then filtered to remove the carbon, and the solution was concentrated. Diethyl ether was then added to the resulting stirring solution until the product was precipitated. The reaction products were analyzed by $^1H$, $^{13}C$, and $^{31}P$ NMR. Table 8 lists the yield of the phosphonium salt formed from each of the N-heterocycles.

TABLE 8

| N-heterocycle | Phosphonium Salt | Yield |
|---|---|---|
| 2-bromo-4-picoline | [4-Picpyphos]Br | 52% |
| 2-bromo-3-aminopyridine | [3-Ampyphos]Br | 40% |
| 2-bromo-4-aminopyridine | [4-Ampyphos]Br | 77% |
| 2-bromo-5-aminopyridine | [5-Ampyphos]Br | 42% |
| 2-bromo-6-acylpyridine | [6-Acepyphos]Br | 51% |
| 2-bromoquinoline | [Quinpyphos]Br | 80% |

Example 10

Figure 14:
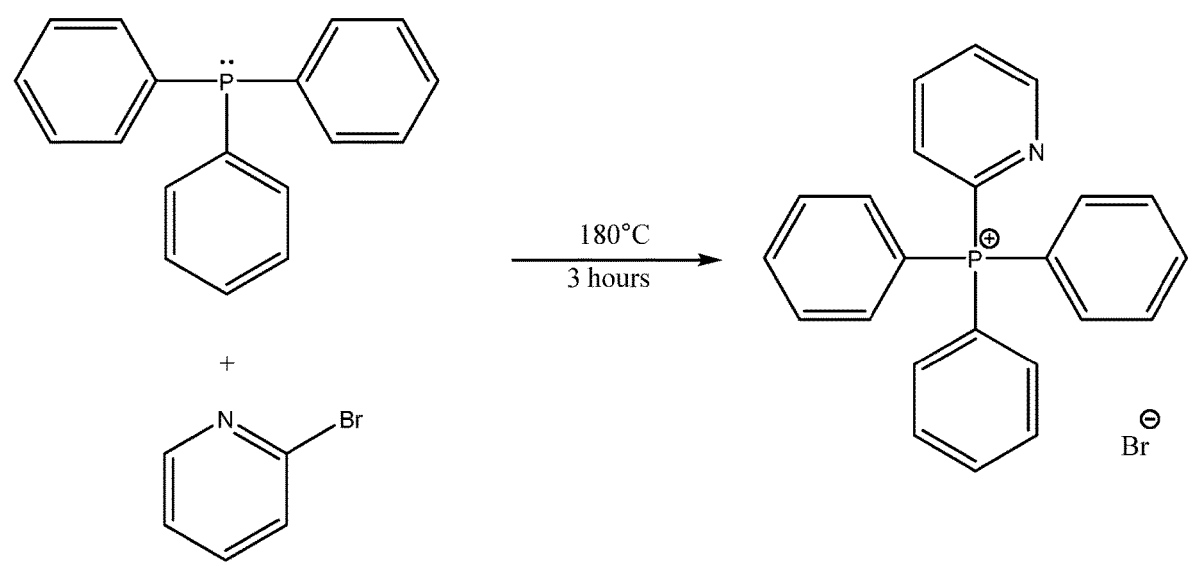
FIG. 14 illustrates the synthesis of the phosphonium salt described in Example 10.

Referring to FIG. 14, 18 mmol of triphenylphosphine was placed in a thick walled pressure vessel equipped with a Teflon screw cap. To this vessel was also added 18 mmol of 2-bromopyridine. The mixture was heated for 3 hours at 180° C. When the mixture was cooled, the residue was dissolved in dichloromethane and stirred with decolorizing carbon. The mixture was then filtered to remove the carbon. Diethyl ether was then added to the resulting solution until the product was precipitated. The yield of [Mopyphos]Br in this reaction was 92%. The reaction product was analyzed by $^1H$, $^{13}C$, and $^{31}P$ NMR, as well as X-ray crystallography.

The experiments in Examples 8 and 10 involved closely analogous reactions with the main difference being the phosphine ingredient: Example 8 used diphenyl(2-pyridyl)phosphine and Example 10 used triphenylphosphine. These experiments resulted in closely analogous yields of the phosphonium salts synthesized when each phosphine ingredient reacted with 2-bromopyridine: 88% yield of [Dipyphos]Br in Example 8 and 92% yield of [Mopyphos]Br in Example 10. Accordingly, the yield of the phosphonium salt synthesized by reacting diphenyl(2-pyridyl)phosphine with an $R_4$—X compound is expected to be closely analogous to the yield of the phosphonium salt synthesized by reacting triphenylphosphine with the same $R_4$—X compound. In other words, closely analogous yields of phosphonium salts are expected when a given $R_4$—X compound is reacted with either diphenyl(2-pyridyl)phosphine or triphenylphosphine in these reactions. However, to obtain similar yields, reactions with diphenyl(2-pyridyl)phosphine must be run for longer times, as exhibited in the 18 hour run time for Example 8 and the 3 hour run time for Example 10.

Figure 15:
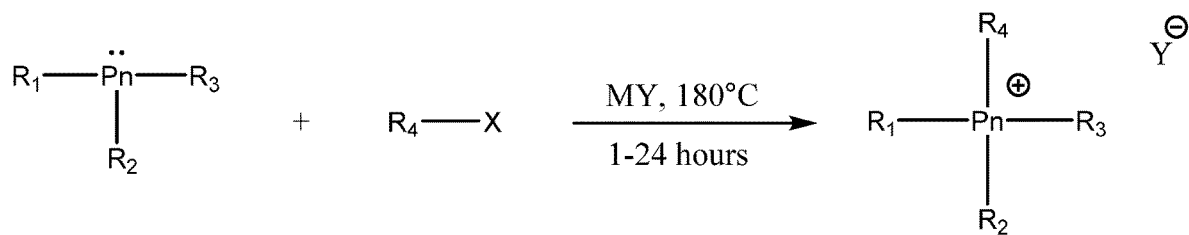
FIG. 15 illustrates the synthesis of pnictogenium salts in the presence of another salt.
Figure 16:
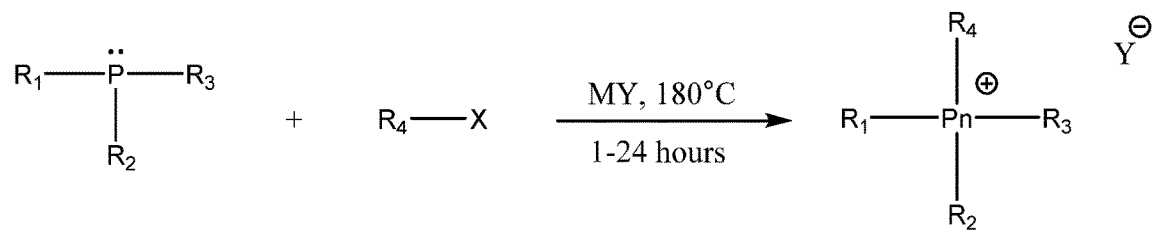
FIG. 16 illustrates the synthesis of phosphonium salts in the presence of another salt.

With reference to FIGS. 15 and 16, the pnictogenium salts used in the synthesis described above may be produced by reacting a compound of the formula $Pn(R_1)(R_2)(R_3)$, including a compound of the formula $P(R_1)(R_2)(R_3)$ as shown in FIG. 16, with $R_4X$ in the presence of salt MY. This process synthesizes pnictogenium salts with various anions.

Example 11

Figure 17:
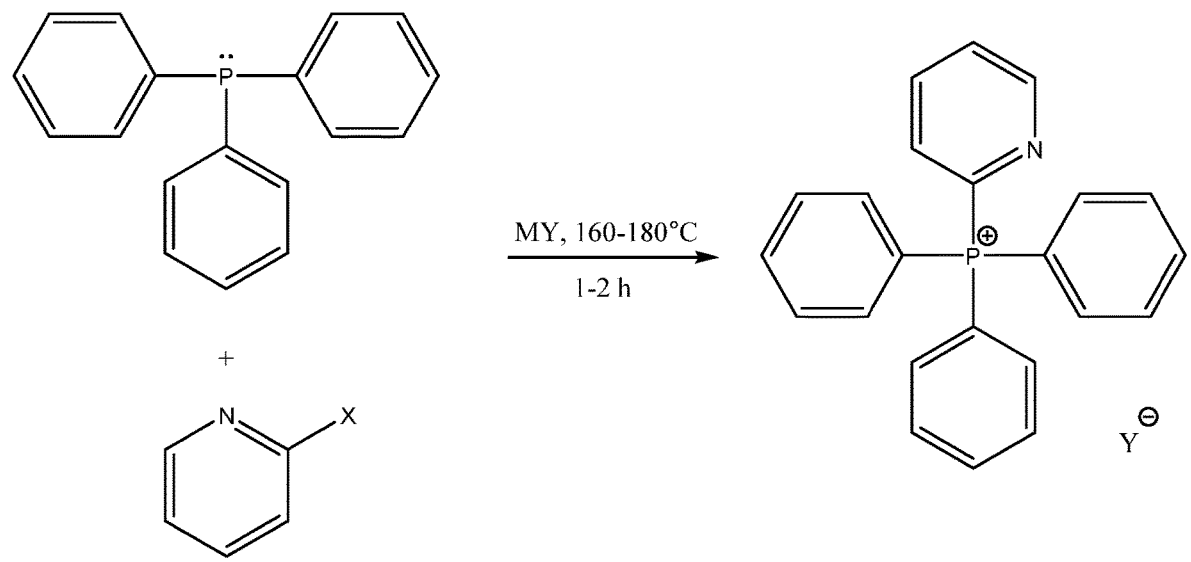
FIG. 17 illustrates the synthesis of the phosphonium salt described in Example 11.

Referring now to FIG. 17 and Table 9 below, 3.8 mmol of triphenylphosphine was placed in a thick walled pressure vessel equipped with a Teflon screw cap. To this vessel was also added 3.8 mmol of 2-bromopyridine or 3.8 mmol of 2-chloropyridine with 3.8 mmol of each of the MY salts as listed in Table 9. In these experiments, the $R_4X$ ingredients were 2-bromopyridine and 2-chloropyridine such that X was Br$^-$ and Cl$^-$. Other acceptable X atoms in the $R_4X$ ingredient include I$^-$ and any other halogens. The mixture was heated for the time and at the temperature indicated in Table 9. When the mixture was cooled, the residue was dissolved in 50 mL of dichloromethane and stirred with decolorizing carbon. After filtration, the dichloromethane layer was washed with distilled water (3×25 mL) and the organic layer concentrated. Diethyl ether was then added to the resulting solution until the product was precipitated. The [Mopyphos]Y salt product was collected by filtration and dried. The reaction product was analyzed by $^1$H, $^{13}$C, and $^{31}$P NMR, as well as X-ray crystallography and $^{19}$F NMR, where appropriate. Table 9 lists the yield of the [Mopyphos]Y salt product synthesized in these reactions from each listed MY salt. While this Example 11 used triphenylphosphine as the phosphine ingredient, the same or similar yield of the analogous phosphonium salt is expected with the use of diphenyl(2-pyridyl)phosphine as the phosphine ingredient due to the similarity in the reactivity and properties of triphenylphosphine and diphenyl(2-pyridyl)phosphine as demonstrated in Example 10.

TABLE 9

| X = Cl; 160° C., 2 hour | X = Br; 180° C., 1 hour |
|---|---|
| For LiTf$_2$N; yield (45%) | For LiTf$_2$N; yield (88%) |
| For KTf$_2$N; yield (4%) | For KTf$_2$N; yield (61%) |
| For KTf$_2$N/LiBr; yield (19%) | For KTf$_2$N/LiBr; yield (56%) |
| For LiBF$_4$; yield (50%) | For LiBF$_4$; yield (62%) |
| For NaBF$_4$; yield (2%) | For NaBF$_4$; yield (25%) |
| For NaBF$_4$/LiBr; yield (69%) | For NaBF$_4$/LiBr; yield (74%) |

Example 12

Figure 18:
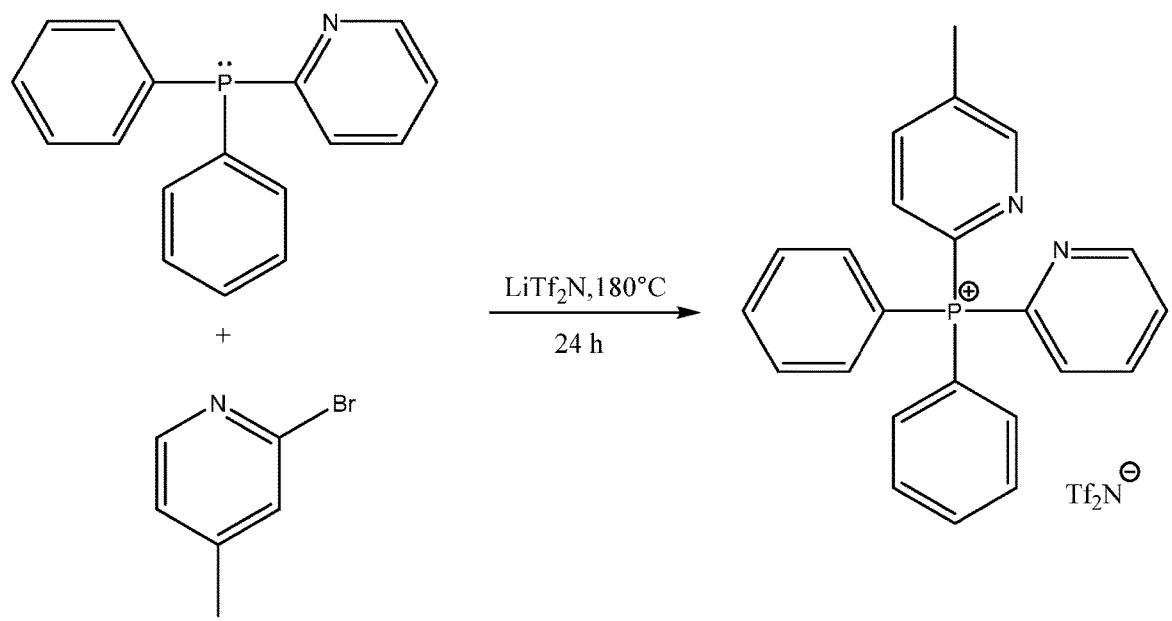
FIG. 18 illustrates the synthesis of the pnictogenium salt described in Example 12.

With reference to FIG. 18, 4.0 mmol of diphenyl(2-pyridyl)phosphine was placed in a thick walled pressure vessel equipped with a Teflon screw cap. To this vessel was also added 4.0 mmol of 2-bromo-4-methyl pyridine and 4.0 mmol of lithium bistriflimide (i.e., the salt of the formula MY). The mixture was heated for 24 hours at 180° C. When the mixture was cooled, the residue was dissolved in 50 mL of dichloromethane and stirred with decolorizing carbon. After filtration, the dichloromethane layer was washed with distilled water (3×25 mL) and the organic layer concentrated. Diethyl ether was then added to the resulting solution until the product was precipitated. The phosphonium salt was collected by filtration and dried. The reaction product was analyzed by $^1$H, $^{13}$C, $^{31}$P NMR and $^{19}$F NMR. The yield of [4-Picpyphos]Tf$_2$N in this reaction was 64%.

Example 13

Figure 19:
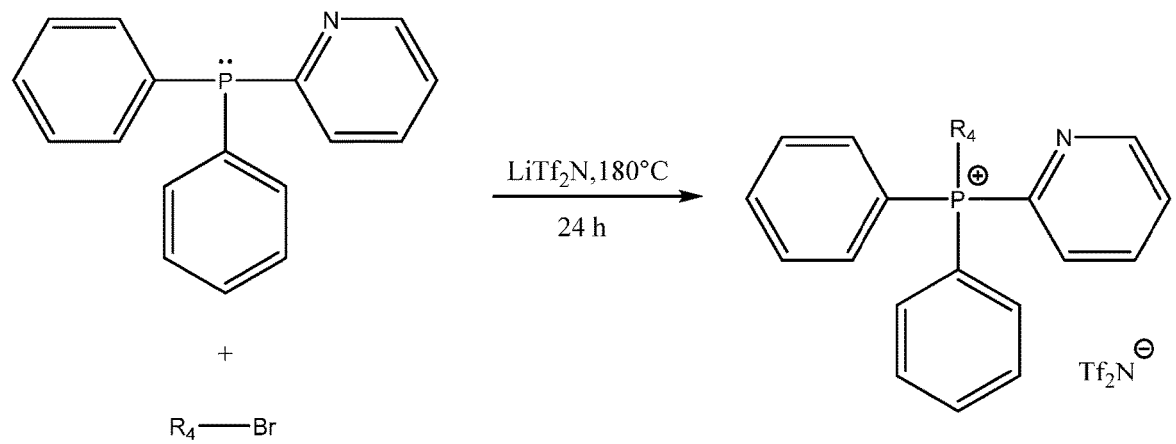
FIG. 19 illustrates the synthesis of the phosphonium salt described in Example 13.

With reference to FIG. 19 and Table 10 below, 3.8 mmol of triphenylphosphine was placed in a thick walled pressure vessel equipped with a Teflon screw cap. To this vessel was also added 3.8 mmol of each of the N-heterocycles listed in Table 10 and 3.8 mmol of lithium bistriflimide (i.e., the salt of the formula MY). The mixture was heated for 24 hours at 180° C. When the mixture was cooled, the residue was dissolved in 50 mL of dichloromethane and stirred with decolorizing carbon. After filtration, the dichloromethane layer was washed with distilled water (3×25 mL) and the organic layer concentrated. Diethyl ether was then added to the resulting solution until the product was precipitated. The phosphonium salt was collected by filtration and dried. The reaction product was analyzed by $^1$H, $^{13}$C, and $^{31}$P NMR, as well as X-ray crystallography and HRMS. Table 10 lists the yield of the salt product formed from each of the N-heterocycles. While this Example 13 used triphenylphosphine as the phosphine ingredient, the same or similar yield of the analogous phosphonium salt is expected with the use of diphenyl(2-pyridyl)phosphine as the phosphine ingredient due to the similarity in the reactivity and properties of triphenylphosphine and diphenyl(2-pyridyl)phosphine as demonstrated in Example 10.

TABLE 10

| N-heterocycle | Phosphonium Salt | Yield |
|---|---|---|
| 2-bromo-6-picoline | [6-Mopicphos]Tf$_2$N | 54% |
| 2-bromo-5-picoline | [5-Mopicphos]Tf$_2$N | 63% |
| 1-bromo-4-picoline | [4-Mopicphos]Tf$_2$N | 53% |
| 2-bromo-4-aminopyridine | [4-Moamphos]Tf$_2$N | 54% |
| 2-bromoquinoline | [Moquinphos]Tf$_2$N | 90% |

Example 14

Figure 20:
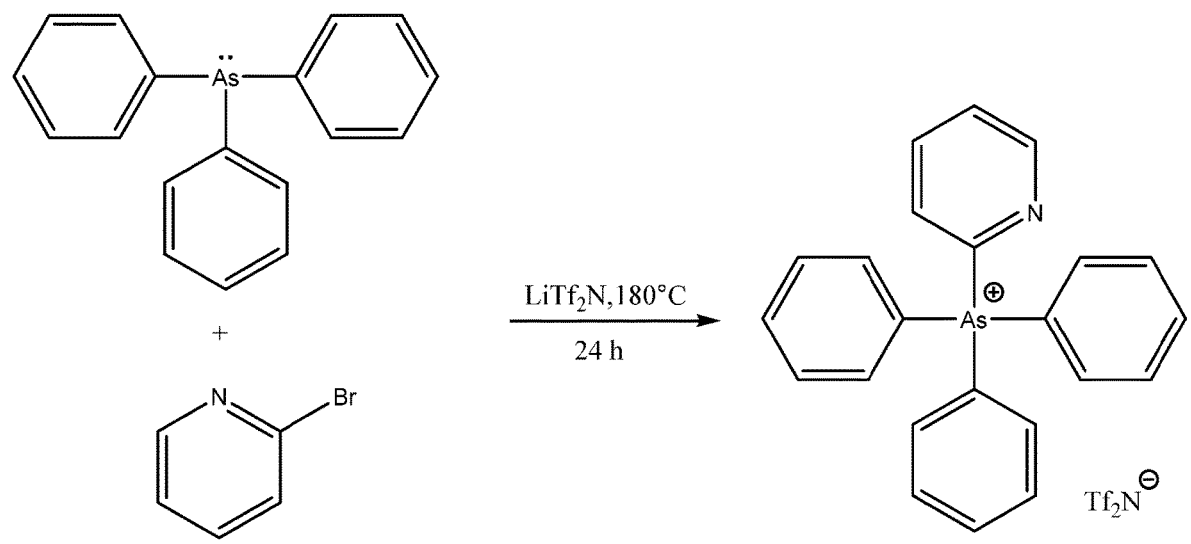
FIG. 20 illustrates the synthesis of the phosphonium salt described in Example 14.

With reference to FIG. 20, the synthesis of another pnictogenium salt is illustrated. Specifically, 3.3 mmol of triphenylarsine was placed in a thick walled pressure vessel equipped with a Teflon screw cap. To this vessel was also added 3.3 mmol of 2-bromopyridine and 3.3 mmol of lithium bistriflimide. The mixture was heated for 24 hours at 180° C. When the mixture was cooled, the residue was dissolved in 50 mL of dichloromethane and stirred with decolorizing carbon. After filtration, the dichloromethane layer was washed with distilled water (3×25 mL) and the organic layer concentrated. Diethyl ether was then added to the resulting solution until the product was precipitated. The pnictogenium salt was collected by filtration and dried. The yield of [Mopyarse]Tf$_2$N in this reaction was 8.7%. The reaction product was analyzed by $^1$H and $^{13}$C NMR. While this Example 14 used triphenylarsine as the ingredient, the same or similar yield of the analogous pnictogenium salt is expected with the use of diphenyl(2-pyridyl)arsine as an ingredient due to the similarity in the reactivity and properties of triphenylarsine and diphenyl(2-pyridyl)arsine.

Example 15

Figure 21:
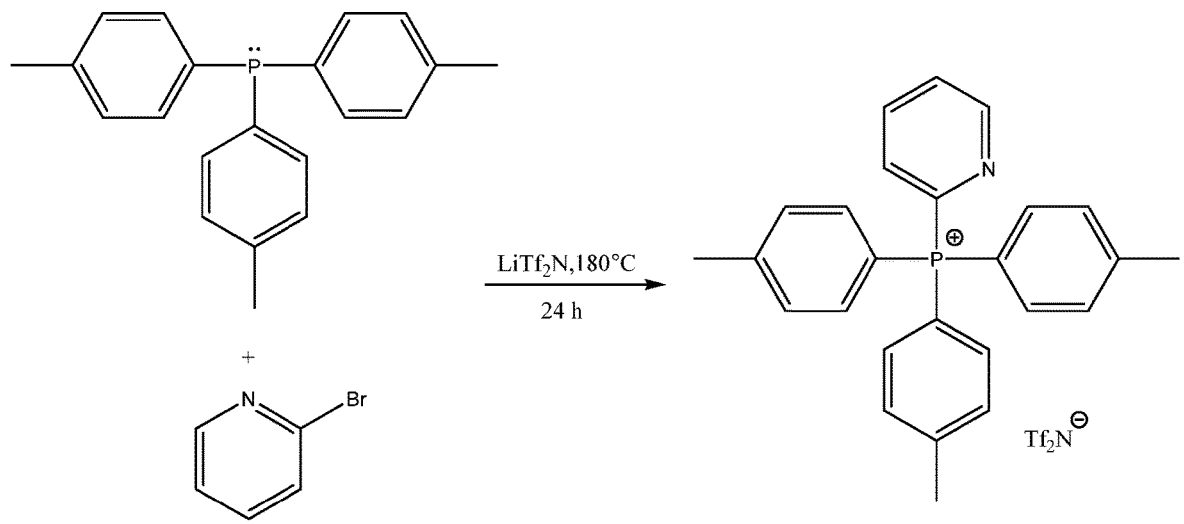
FIG. 21 illustrates the synthesis of the phosphonium salt described in Example 15.

With reference to FIG. 21, 3.3 mmol of tri-p-tolylphosphine was placed in a thick walled pressure vessel equipped with a Teflon screw cap. To this vessel was also added 3.3 mmol of 2-bromopyridine and 3.3 mmol of lithium bistriflimide. The mixture was heated for 24 hours at 180° C. When the mixture was cooled, the residue was dissolved in 50 mL of dichloromethane and stirred with decolorizing carbon. After filtration, the dichloromethane layer was washed with distilled water (3×25 mL) and the organic layer concentrated. Diethyl ether was then added to the resulting solution until the product was precipitated. The phosphonium salt was collected by filtration and dried. The yield of $^{ptol}$[Mopyphos]Tf$_2$N in this reaction was 63%. The reaction product was analyzed by $^1$H, $^{13}$C, $^{19}$F, and $^{31}$P NMR. While this Example 15 used tri-p-tolylphosphine as the phosphine ingredient, the same or similar yield of the analogous phosphonium salt is expected with the use of di-p-tolyl(2-pyridyl)phosphine as the phosphine ingredient due to the similarity in the reactivity and properties of tri-p-tolylphosphine and di-p-tolyl(2-pyridyl)phosphine.

The pnictogenium salts, including the phosphonium salts, described above may be modified by anion exchange.

Example 16

Figure 22:
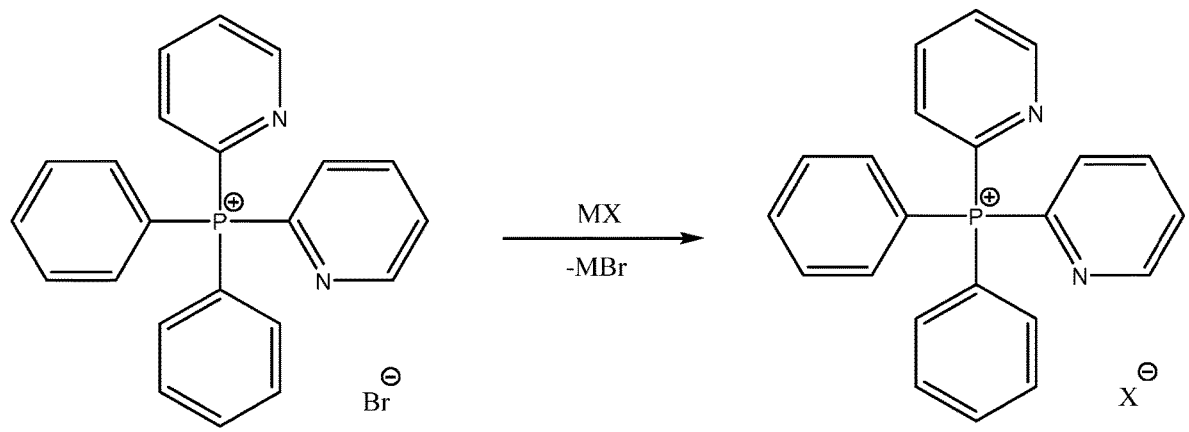
FIG. 22 illustrates the synthesis of phosphonium salts via anion exchange in Example 16.

Referring now to FIG. 22 and Table 11 below, 10 mmole of [Dipyphos]Br was suspended in 50 mL of water. The suspension dissolved upon heating to approximately 100° C. To this solution was added a solution of 1.1 equivalents of each MX salt listed in Table 11 dissolved in 50 mL of hot water. [Dipyphos]X immediately precipitated out. The mixture was extracted three times with 50 mL portions of dichloromethane. The organic fractions were combined, dried over anhydrous magnesium sulfate, and concentrated to 50 mL. Diethylether was added to the solution until [Dipyphos]X precipitated. The solid was collected via filtration and dried. Product was analyzed by $^1H$, $^{13}C$, and $^{31}P$ NMR, as well as $^{19}F$ NMR, where applicable. Table 11 lists the yield of the [Dipyphos]X salt produced with each MX salt. In the MX salt, M may be H$^+$, Li$^+$, Na$^+$, K$^+$, Rb$^+$, or Cs$^+$ and X is an anion, including but not limited to $N(SO_2CF_3)_2^-$, $BF_4^-$, $PF_6^-$, $B(C_6H_5)4^-$.

TABLE 11

| | |
|---|---|
| For LiN(SO$_2$CF$_3$)$_2$: Yield = 90% | For NaB(C$_6$H$_5$)$_4$: Yield = 85% |
| For NaBF$_4$: Yield = 70% | For NaPF$_6$: Yield = 80% |

Example 17

Figure 23:
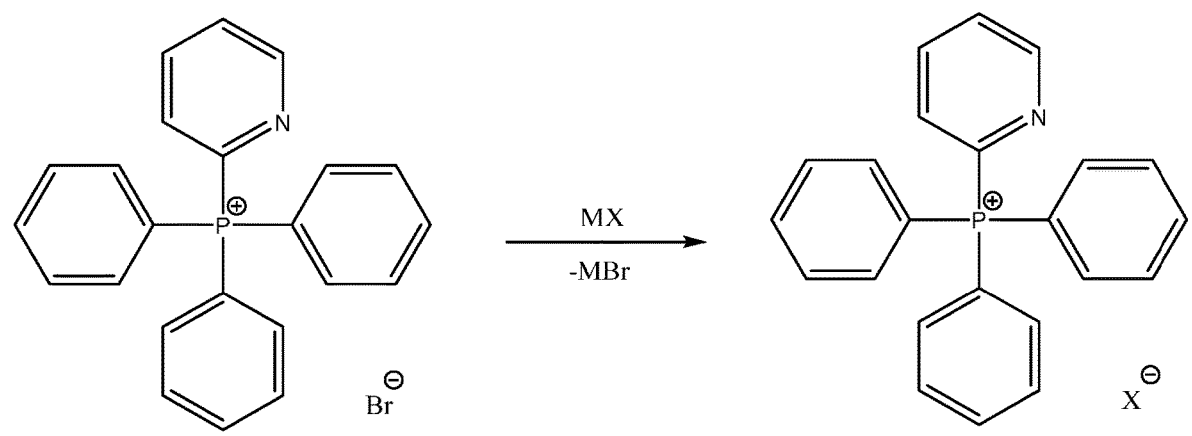
FIG. 23 illustrates the synthesis of phosphonium salts via anion exchange in Example 17.

Referring now to FIG. 23 and Table 12 below, 3.8 mmole of [Mopyphos]Br was suspended in 50 mL of water. The suspension dissolved upon heating to approximately 100° C. To this solution was added a solution of 1.1 equivalents of each MX salt listed in Table 12 dissolved in 50 mL of hot water. [Mopyphos]X immediately precipitated out. The mixture was extracted three times with 50 mL portions of dichloromethane. The organic fractions were combined, dried over anhydrous magnesium sulfate, and concentrated to 50 mL. Diethylether was added to the solution until [Mopyphos]X precipitated. The solid was collected via filtration and dried. Product was analyzed by $^1H$, $^{13}C$, and $^{31}P$ NMR, as well as $^{19}F$ NMR, where applicable. Table 12 lists the yield of the [Mopyphos]X salt produced with each MX salt. In the MX salt, M may be H$^+$, Li$^+$, Na$^+$, K$^+$, Rb$^+$, or Cs$^+$ and X is an anion, including but not limited to $N(SO_2CF_3)_2^-$, $BF_4^-$, $PF_6^-$, $B(C_6H_5)4^-$.

TABLE 12

| | |
|---|---|
| For KN(SO$_2$CF$_3$)$_2$: Yield = 82% | For potassium acesulfame: Yield = 68% |
| For NaBF$_4$: Yield = 80% | For sodium saccharinate: Yield = 72% |
| For NaB(C$_6$H$_5$)$_4$: Yield = 68% | |

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the term "heteroatom" refers to an element other than carbon, including, but not limited to, nitrogen (N), oxygen (O), silicon (Si), phosphorus (P), boron (B), sulfur (S), and halogen atoms, unless otherwise stated.

As used herein, the term "halogen" refers to fluorine (F), chlorine (Cl), bromine (Br), and iodine (I).

As used herein, "pnictogen" means nitrogen (N), phosphorus (P), arsenic (As), antimony (Sb), bismuth (Bi), and moscovium (Mc).

As used herein, the term "alkyl" refers to a fully saturated branched or unbranched hydrocarbon moiety having up to 10 carbon atoms. Unless otherwise provided, alkyl refers to hydrocarbon moieties having 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "cycloalkyl" refers to a saturated hydrocarbon mono- or polycyclic system having 3 to 30 carbon atoms. Examples of cycloalkyl include, but are not limited to, cyclopropyl, cyclobutyl, cyclopentyl, cyclohexyl, cycloheptyl, cyclooctyl, and adamantyl, and the like.

As used herein, the terms "heteroalkyl" and "heteroaliphatic" refers to a straight or branched hydrocarbon chain containing one or more heteroatoms in the chain backbone. The heteroalkyl group may have 1 to 20 carbon atoms or more than 20 carbon atoms. The heteroalkyl group may also have 1 to 9 carbon atoms or 1 to 4 carbon atoms. Nonlimiting examples include methylamino, diethylamino, thioethyl, diisopropylamine, diisopropylphosphino, and the like.

As used herein, the term "heterocycloalkyl" refers to a saturated or unsaturated nonaromatic 3-8 membered monocyclic, 7-12 membered bicyclic, or 11-14 membered tricyclic ring system having one or more heteroatoms (such as O, N, S, or Se), unless specified otherwise. Nonlimiting examples include piperidinyl, piperazinyl, pyrrolidinyl, dioxanyl, tetrahydrofuranyl, isoindolinyl, and the like.

As used herein, the term "aryl" refers to an aromatic hydrocarbon group having 6 to 14 carbon atoms in the ring portion. Typically, aryl is monocyclic, bicyclic or tricyclic aryl having 6 to 14 carbon atoms, often 6 to 10 carbon atoms, e.g., phenyl or naphthyl. Phenyl is sometimes preferred. Furthermore, the term "aryl" as used herein, refers to an aromatic substituent which can be a single aromatic ring, or multiple aromatic rings that are fused together. Non-limiting examples include phenyl, naphthyl and 1,2,3,4-tetrahydronaphthyl, provided the tetrahydronaphthyl is connected to the formula being described through a carbon of the aromatic ring of the tetrahydronaphthyl group.

As used herein, the terms "heteroaryl" and "heteroaromatic" refer to a 5 to 14 membered monocyclic-, bicyclic-, or tricyclic-aromatic ring system, having 1 to 8 heteroatoms as ring members; the heteroatoms are selected from N, O and S. Typically, the heteroaryl is a 5 to 10 membered ring system, e.g., a 5 to 6 membered monocyclic or an 8 to 10 membered bicyclic group. Typical heteroaryl groups include 2- or 3-thienyl, 2- or 3-furyl, 2- or 3-pyrrolyl, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2,3-triazolyl), 1- or 2- or 3-tetrazolyl, 2-, 3-, or 4-pyridyl, 3- or 4-pyridazinyl, 2-pyrazinyl, 2-, 4-, or 5-pyrimidinyl, and the like.

The terms "heteroaryl" and "heteroaromatic" also refer to a group in which a heteroaromatic ring is fused to one or more aryl, cycloalkyl, or heterocyclyl rings, where the radical or point of attachment to the formula of interest is on a heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, and the like.

As used herein, the term "aralkyl" refers to an alkyl group which is substituted with an aryl group. Nonlimiting examples of aralkyls include benzyl, phenethyl, and the like.

As used herein, the term "alkoxy" refers to the group —OR wherein R is an alkyl. Nonlimiting examples of alkoxy groups include methoxy, ethoxy, n-propoxy, 1-methylethoxy (isopropoxy), n-butoxy, iso-butoxy, sec-butoxy, and tert-butoxy, and the like.

As used herein, the term "amino" refers to a primary, secondary, or tertiary amine which may be optionally substituted. Specifically included are secondary or tertiary amine nitrogen atoms which are members of a heterocyclic ring. Also specifically included, for example, are secondary or tertiary amino groups substituted by an acyl moiety. Nonlimiting examples of an amino group include —NR'R" wherein each of R' and R" is independently hydrogen, alkyl, aryl, aralkyl, alkaryl, cycloalkyl, acyl, heteroalkyl, heteroaryl, heterocycyl, or the like.

As used herein, the term "organosilyl" refers to a group consisting of three groups bonded to a silicon atom. Nonlimiting examples of organosilyl groups include trimethylsilyl, triethylsilyl, t-butyldiphenylsilyl, tris(dimethylamino)silyl, tris(trimethylsilyl)silyl, and the like.

As used herein, the term "substituted" refers to a compound or moiety in which at least one hydrogen atom is replaced by a substituent. Nonlimiting examples of substituents include an alkyl group, an alkenyl group, an alkynyl group, an aryl group, an alkylaryl group, an alkoxy group, a heteroalkyl group, a heteroaryl group, a cycloalkyl group, a cycloalkenyl group, a cycloalkynyl group, a heterocycloalkyl group, a halogen (—F, —Cl, —Br, or —I), a hydroxyl group (—OH), a nitro group (—NO$_2$), a cyano group (—CN), an amino group (—NRR', wherein R and R' are independently hydrogen or a C$_1$ to C$_6$ alkyl group), an azido group (—N$_3$), an amidino group, a hydrazino group (—NHNH$_2$), a hydrazono group, an aldehyde group, a carbamoyl group (—C(O)NH$_2$), a thiol group (—SH), an ester group (—COOR, wherein R is a C$_1$ to C$_6$ an alkyl group or a C$_6$ to C$_{12}$ aryl group), a carboxyl group (—COOH) or a salt thereof, a sulfonic acid group (—SO$_3$H) or a salt thereof (—SO$_3$M, wherein M is an organic or inorganic cation), a phosphoric acid group (—PO$_3$H$_2$) or a salt thereof (—PO$_3$MH or —PO$_3$M$_2$, wherein M is an organic or inorganic cation), or a combination thereof.

As used herein, the term "optionally substituted" indicates that a group being described can be unsubstituted or it can be substituted. Substituted groups are not intended to encompass numbers, placement, or selections of substituent groups that would result in a compound that is not expected to be stable in water at room temperature for at least long enough to extrude R$_3$-R$_4$ under the claimed compositions. When multiple substituents are present, the substituents are selected independently unless otherwise indicated, so where 2 or 3 substituents are present, for example, those substituents may be the same or different.

As used herein, the term "monocyclic" refers to a structure comprising three or more atoms that are connected to form a ring. These rings may be aliphatic or aromatic in nature, and are optionally substituted. Nonlimiting examples include cyclopropyl, phenyl, tolyl, cyclohexyl, pyridyl, and the like.

As used herein, the term "polycyclic" refers to a structure that contains two or more ring structures, which can either be attached at a single atom, or fused, sharing one or more edges. The rings may be aliphatic, aromatic, or a mix of aliphatic and aromatic rings. Nonlimiting examples include phenylpyridyl, bipyridyl, cyclohexylpyridyl, quinolinyl, norbornyl benzo[a]pyreneyl, adamantly, and the like.

As used herein, the term "ambient temperature" means room temperature or an indoor temperature. Nonlimiting examples of ambient temperatures include temperatures in the range of 20° C. to 30° C.

As used herein, the term "Lewis acid" means any species capable of accepting a pair of electrons from a donor atom.

As used herein, the term "nucleophile" means any species capable of donating an electron pair to the pnictogenium species or the phosphonium species.

As used herein, the terms "a" or "an" are defined as one or more than one. The term "plurality," as used herein, is defined as two or more than two. The term "another," as used herein, is defined as at least a second or more. The terms "comprises," "comprising," or any other variation thereof are intended to cover a non-exclusive inclusion, such that a process, method, article, or apparatus that comprises a list of elements does not include only those elements, but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including," "having," or "featuring," as used herein, are defined as comprising (i.e., open language). The term "coupled," as used herein, is defined as connected, although not necessarily directly, and not necessarily mechanically. As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. Relational terms such as first and second, top and bottom, right and left, and the like may be used solely to distinguish one item or action from another item or action without necessarily requiring or implying any actual such relationship or order between such entities or actions.

The foregoing description and accompanying drawings illustrate the principles, exemplary embodiments, and modes of operation of the invention. However, the invention should not be construed as being limited to the particular embodiments discussed above. Many modifications of the embodiments described herein will come to mind to one skilled in the art having the benefit of the teaching presented in the foregoing descriptions and the associated drawings. Accordingly, it should be appreciated that variations to those embodiments can be made by those skilled in the art without departing from the scope of the invention.

We claim:

1. A method of synthesizing a bis-N-heteroaromatic compound, comprising the steps of:

reacting a phosphonium salt of the formula

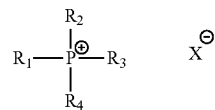

with a Lewis acid, in the presence of a nucleophile, to form a bis-N-heteroaromatic compound of the formula R$_3$-R$_4$;

wherein R$_1$ and R$_2$ are individually selected from the group consisting of hydrogen, alkyl, heteroalkyl, aryl, heteroaryl, aralkyl, alkoxy, amino, and organosilyl;
wherein $R_1$ or $R_2$ optionally forms a covalent bond with $R_3$ or $R_4$ in the phosphonium salt;
wherein $R_3$ and $R_4$ are each an optionally substituted monocyclic or polycyclic N-heteroaromatic ring system containing between 5 and 14 atoms, with at least one nitrogen atom in a position adjacent to the ipso carbon and each of the other members of the ring optionally substituted with a substituent individually selected from the group consisting of alkyl, heteroalkyl, aryl, heteroaryl, alkoxy, and amino;
wherein X is an anion;
wherein the bis-N-heteroaromatic compound includes a first heteroaromatic ring system having a carbon atom bonded to a carbon atom in a second heteroaromatic ring system; and wherein a nitrogen atom is adjacent to the bonded carbon atom in a ring of the first heteroaromatic ring system and a nitrogen atom is adjacent to the bonded carbon atom in a ring of the second heteroaromatic ring system.

2. The method of claim 1, wherein the Lewis acid is $H^+$, a monovalent metal, a divalent metal, or a trivalent metal.

3. The method of claim 1, wherein the nucleophile is a primary, secondary, or tertiary amine.

4. The method of claim 1, wherein the reaction occurs at ambient temperature.

5. The method of claim 1, wherein a yield of the bis-N-heteroaromatic compound is greater than 20%.

6. The method of claim 5, wherein the yield of the bis-N-heteroaromatic compound is greater than 20% in less than 72 hours.

7. The method of claim 5, wherein the yield of the bis-N-heteroaromatic compound is greater than 20% in less than 24 hours.

8. The method of claim 5, wherein the yield of the bis-N-heteroaromatic compound is greater than 20% in less than 8 hours.

9. The method of claim 5, wherein the yield of the bis-N-heteroaromatic compound is greater than 20% in less than 1 hour.

10. The method of claim 1, wherein $R_1$ is not a heteroaromatic group and $R_2$ is not a heteroaromatic group.

11. The method of claim 1, wherein the phosphonium salt is produced by reacting a compound with the formula $P(R_1)(R_2)(R_3)$ with $R_4X$.

12. The method of claim 1, wherein the phosphonium salt is produced by reacting the compound with the formula

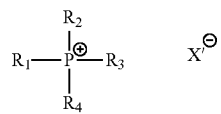

with MX, wherein M is $H^+$, $Li^+$, $Na^+$, $K^+$, $Rb^+$, or $Cs^+$; and wherein X' is an anion.

13. The method of claim 1, wherein $R_1$ and $R_2$, taken together, form an optionally substituted ring consisting of 3-10 backbone atoms; wherein the ring optionally comprises one or two heteroatoms beyond the phosphorus to which $R_1$ and $R_2$ are bonded.

14. A method of synthesizing a bis-Pn-heteroaromatic compound, comprising the steps of:
reacting a pnictogenium salt of the formula

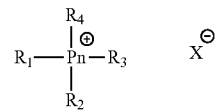

with a Lewis acid, in the presence of a nucleophile, to form a bis-Pn-heteroaromatic compound of the formula $R_3$-$R_4$;
wherein $R_1$ and $R_2$ are individually selected from the group consisting of hydrogen, alkyl, heteroalkyl, aryl, heteroaryl, aralkyl, alkoxy, amino, and organosilyl;
wherein $R_1$ or $R_2$ optionally forms a covalent bond with $R_3$ or $R_4$ in the pnictogenium salt;
wherein $R_3$ and $R_4$ are each an optionally substituted monocyclic or polycyclic Pn-heteroaromatic ring system containing between 5 and 14 atoms, with at least one pnictogen atom in a position adjacent to the ipso carbon and each of the other members of the ring optionally substituted with a substituent individually selected from the group consisting of alkyl, heteroalkyl, aryl, heteroaryl, alkoxy, and amino;
wherein Pn is a pnictogen and X is an anion;
wherein the bis-Pn-heteroaromatic compound includes a first heteroaromatic ring system having a carbon atom bonded to a carbon atom in a second heteroaromatic ring system; and wherein a pnictogen atom is adjacent to the bonded carbon atom in a ring of the first heteroaromatic ring system and a pnictogen atom is adjacent to the bonded carbon atom in a ring of the second heteroaromatic ring system.

15. The method of claim 14, wherein the Lewis acid is $H^+$, a monovalent metal, a divalent metal, or a trivalent metal.

16. The method of claim 14, wherein the nucleophile is a primary, secondary, or tertiary amine.

17. The method of claim 14, wherein the reaction occurs at ambient temperature.

18. The method of claim 14, wherein a yield of the bis-Pn-heteroaromatic compound is greater than 20%.

19. The method of claim 18, wherein the yield of the bis-Pn-heteroaromatic compound is greater than 20% in less than 72 hours.

20. The method of claim 18, wherein the yield of the bis-Pn-heteroaromatic compound is greater than 20% in less than 24 hours.

21. The method of claim 18, wherein the yield of the bis-Pn-heteroaromatic compound is greater than 20% in less than 8 hours.

22. The method of claim 18, wherein the yield of the bis-Pn-heteroaromatic compound is greater than 20% in less than 1 hour.

23. The method of claim 14, wherein $R_1$ is not a heteroaromatic group and $R_2$ is not a heteroaromatic group.

24. The method of claim 14, wherein the pnictogenium salt is produced by reacting a compound with the formula $Pn(R_1)(R_2)(R_3)$ with $R_4X$.

25. The method of claim 14, wherein the pnictogenium salt is produced by reacting the compound with the formula

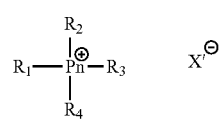

with MX, wherein M is $H^+$, $Li^+$, $Na^+$, $K^+$, $Rb^+$, or $Cs^+$; and wherein X' is an anion.

26. The method of claim 14, wherein $R_1$ and $R_2$, taken together, form an optionally substituted ring consisting of 3-10 backbone atoms; wherein the ring optionally comprises one or two heteroatoms beyond the pnictogen to which $R_1$ and $R_2$ are bonded.

* * * * *